US00PP26738P3

(12) United States Plant Patent

Klemm et al.

(10) Patent No.: US PP26,738 P3

(45) Date of Patent: May 17, 2016

(54) *DIANTHUS* PLANT NAMED 'KLEDP13122'

(50) Latin Name: *Dianthus caryophyllus*
Varietal Denomination: KLEDP13122

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 107 days.

(21) Appl. No.: 14/120,256

(22) Filed: May 13, 2014

(65) Prior Publication Data

US 2015/0334894 P1 Nov. 19, 2015

(51) Int. Cl.
*A01H 5/02* (2006.01)

(52) U.S. Cl.
USPC ..... Plt./273

(58) Field of Classification Search
USPC ..... Plt./276, 277, 273
See application file for complete search history.

*Primary Examiner* — June Hwu
(74) *Attorney, Agent, or Firm* — Barbara Campbell; Bethany R. Roahrig; Cochran Freund & Young, LLC

(57) ABSTRACT

A new *Dianthus* plant particularly distinguished by double, violet bi-color flowers and an upright form, is disclosed.

1 Drawing Sheet

Genus and species: *Dianthus caryophyllus*.
Variety denomination: 'KLEDP13122'.

BACKGROUND OF THE NEW PLANT

The present invention comprises a new and distinct variety of *Dianthus*, botanically known as *Dianthus caryophyllus*, and hereinafter referred to by the variety name 'KLEDP13122'. 'KLEDP13122' originated from a cross-pollination conducted in June 2006 in Stuttgart, Germany between the proprietary female *Dianthus* variety 'DCP 2004 0017' (unpatented) and the proprietary male *Dianthus* variety 'DCP 2005 0139' (unpatented).

The seeds from the cross were sown and plants were grown in a greenhouse for evaluation, where an individual plant designated 'KLEDP13122' was selected from the group of plants in May 2006 in Stuttgart, Germany. In June 2007, 'KLEDP13122' was first vegetatively propagated by vegetative stem cuttings. 'KLEDP13122' was found to reproduce true to type in successive generations of asexual propagation in Stuttgart, Germany via vegetative stem cuttings.

SUMMARY

The following are the most outstanding and distinguishing characteristics of this new variety when grown under normal horticultural practices in Stuttgart, Germany.

1. Double, violet bi-color flowers; and
2. An upright form.

CROSS REFERENCE TO RELATED APPLICATIONS

Plant Breeders Rights for this variety have been filed with the European Community Plant Variety Rights Office on Jun. 28, 2013, Application No. 2013/1746. 'KLEDP13122' has not been sold or made publicly available more than one year prior to the filing of the instant application.

DESCRIPTION OF THE PHOTOGRAPH

This new *Dianthus* plant is illustrated by the accompanying photograph of a plant approximately 5-month old and grown in a glass greenhouse in Stuttgart, Germany.

The photograph shows the whole plant, including the flowers and foliage and buds and was taken in April 2011 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDP13122'. The data which define these characteristics were collected from asexual reproductions carried out in Stuttgart, Germany. Data was collected on 5-month old plants grown in a greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP13122'.

Parentage:
- *Female parent*.—The proprietary female *Dianthus* variety 'DCP 2004 0017' (unpatented).
- *Male parent*.—The proprietary male *Dianthus* variety 'DCP 2005 0139' (unpatented).

Plant:
- *Propagation type*.—Vegetative stem cuttings.
- *Time to produce a rooted young plant*.—14 to 16 days.
- *Root description*.—White, fine.
- *Rooting habit*.—Lanceolate.
- *Plant form*.—Potted plant, upright.
- *Plant height*.—13.0 cm to 15.0 cm.
- *Plant diameter or spread*.—16.0 cm to 18.0 cm.

Lateral branches:

*Length.*—8.0 cm to 10.0 cm.

*Diameter.*—4.0 mm.

*Internode length.*—1.5 cm.

*Number of internodes per lateral branch.*—4.

*Node length.*—0.4 cm to 0.5 cm.

*Node diameter.*—0.5 cm.

*Texture.*—Smooth.

*Color.*—RHS 137A. Flower buds and flowers present along the lateral branch. Stem is hollow.

Foliage:

*Arrangement.*—Opposite.

*Length.*—4.0 cm to 6.0 cm.

*Width.*—7.0 cm to 9.0 cm.

*Shape.*—Lanceolate.

*Apex.*—Acute.

*Base.*—Obtuse.

*Margin.*—Entire.

*Texture (both upper and lower surfaces).*—Smooth.

*Immature leaf color.*—Upper surface: RHS 137C. Lower surface: RHS 138A.

*Mature leaf color.*—Upper surface: RHS 139A. Lower surface: RHS 137A.

*Venation pattern.*—Palmate.

*Venation color (both upper and lower surfaces).*—RHS 139A.

Flowers:

*Flower type and habit.*—Double, round, and small sprays.

*Fragrance.*—Present, strong.

*Natural flowering season.*—Spring to fall.

*Flower longevity on the plant.*—10 to 12 days.

*Position of the flowers in relation to the foliage.*—Slightly above.

*Number of flowers per spray.*—3 to 5.

*Buds.*—Length: 1.6 cm to 1.8 cm. Diameter: 0.8 cm to 1.0 cm. Shape: Elliptic. Color: RHS 143C and RHS 183A. Extrusion of the styles in the bud stage: Not present.

*Corolla.*—Quantity of petals and arrangement: 10 to 12 petals arranged in several whorls. Corolla height: 1.5 cm to 2.0 cm. Petal length: 3.5 cm. Petal width: 2.0 cm to 2.5 cm. Petal shape: Spoon-shaped. Petal apex: Obtuse. Petal base: Acute. Petal margin: Crenate and depth is medium. Petal texture (both upper and lower surfaces): Smooth. Petal color: Immature: Upper surface: RHS N78A and RHS 58B. Lower surface: RHS N78C. Mature: Upper surface: RHS 76B and RHS 72B with RHS 64A at base of petal. Lower surface: RHS 69C.

*Calyx.*—Quantity of sepals and arrangement: Composed of 5 fused sepals. Calyx height: 1.6 cm to 1.8 cm. Calyx diameter (at the apex): 0.8 cm to 1.8 cm. Calyx shape: Campanulate. Sepal texture (both upper and lower surfaces): Smooth. Sepal color: Upper surface: RHS N137C. Lower surface: RHS 144A.

*Epicalyx.*—Adpressed; approximate length is 0.6 cm; approximate width is 0.6 cm; color is RHSS 136B and RHS 184A; and apex shape is acuminate.

Peduncles: Length: 12.0 cm to 14.0 cm. Diameter: 0.2 cm. Strength: Moderate. Texture: Smooth. Color: RHS N137B.

Reproductive organs:

*Stamens.*—Quantity per flower: 9 to 11. Filament length: 2.5 cm. Filament color: RHS 73A. Anther length: 0.2 cm. Anther diameter: 0.1 cm. Anther color: RHS 93D. Pollen amount: Abundant.

*Pistils.*—Quantity per flower: 1. Pistil length: 0.1 cm. Style length: 1.8 cm. Style color: RHS 49D. Stigma shape: Filamentous. Stigma color: RHS 73B. Ovary size: 0.5 cm. Ovary shape: Oval. Ovary color: RHS 145B. Ovary surface texture: Smooth.

Fruit and seed set: Seed observed but additional information on seed not available.

Disease and pest/insect resistance: No disease and pest/insect resistance observed.

COMPARISON WITH PARENTAL LINES AND KNOWN VARIETY

'KLEDP13122' is a distinct variety of *Dianthus* and is distinguished from its parents as described in Table 1.

TABLE 1

Comparison with Parental Lines

| Characteristic | 'KLEDP13122' | Female Parent 'DCP 2004 0017' | Male Parent 'DCP 2005 0139' |
|---|---|---|---|
| Flower color | Violet bicolor | Purple | Lavender |

'KLEDP13122' is a distinct variety of *Dianthus* and is most similar to the commercial *Dianthus* variety SuperTrouper™ 'Carmen' (unpatented). Differences between the varieties are described in Table 2.

TABLE 2

Comparison with Similar Variety

| Characteristic | 'KLEDP13122' | SuperTrouper ™ 'Carmen' |
|---|---|---|
| Flower type | Double | Single |
| Flower color | Violet bicolor | Dark-red bicolor |

We claim:

1. A new and distinct variety of *Dianthus* plant designated 'KLEDP13122' as illustrated and described herein.

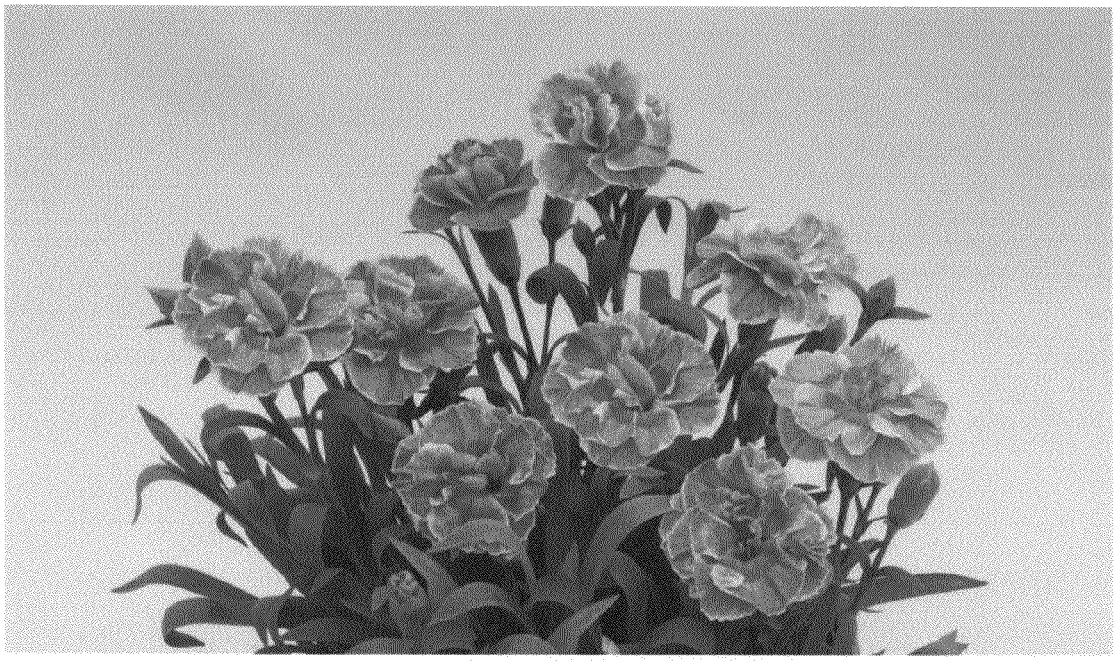

* * * * *